United States Patent [19]

Miura et al.

[11] Patent Number: 5,370,108
[45] Date of Patent: Dec. 6, 1994

[54] ENDOSCOPE

[75] Inventors: Shizuharu Miura; Takayuki Ogino; Hiroyuki Katsurada, all of Tokyo, Japan

[73] Assignee: Asahi Kogaku Kogyo Kabushiki Kaisha, Tokyo, Japan

[21] Appl. No.: 948,499

[22] Filed: Sep. 22, 1992

[30] Foreign Application Priority Data

| Oct. 2, 1991 | [JP] | Japan | 3-255287 |
| Oct. 3, 1991 | [JP] | Japan | 3-256279 |
| Oct. 3, 1991 | [JP] | Japan | 3-256280 |
| Oct. 21, 1991 | [JP] | Japan | 3-271613 |
| Aug. 27, 1992 | [JP] | Japan | 4-228112 |
| Aug. 27, 1992 | [JP] | Japan | 4-228113 |

[51] Int. Cl.$^5$ .......................... A61B 1/00; A61B 1/04
[52] U.S. Cl. ............................... 128/4; 128/6; 385/118
[58] Field of Search ................ 385/118, 117; 606/15, 606/16, 19; 138/130, 133, 125; 128/4, 6

[56] References Cited

U.S. PATENT DOCUMENTS

| 3,417,745 | 12/1968 | Sheldon | 385/117 X |
| 3,572,325 | 3/1971 | Bazell et al. | 128/6 |
| 3,691,001 | 9/1972 | Takahashi et al. | |
| 3,788,304 | 1/1974 | Takahashi | 385/118 X |
| 3,799,151 | 3/1974 | Fukaumi et al. | 128/4 X |
| 3,855,897 | 12/1974 | Takahashi et al. | |
| 4,236,509 | 12/1980 | Takahashi et al. | 128/4 |
| 4,279,245 | 7/1981 | Takagi et al. | 128/4 |
| 4,327,711 | 5/1982 | Takagi | 128/4 |
| 4,699,463 | 10/1987 | D'Amelio et al. | 385/118 |
| 4,708,434 | 11/1987 | Tsuno | 385/118 |
| 4,784,464 | 11/1988 | Ouchi | |
| 4,899,787 | 2/1990 | Ouchi et al. | 128/4 X |
| 4,944,287 | 7/1990 | Takahashi et al. | |
| 4,979,498 | 12/1990 | Oneda et al. | 128/6 |
| 5,058,568 | 10/1991 | Irion et al. | 128/4 |
| 5,073,048 | 12/1991 | Adachi et al. | |
| 5,254,107 | 10/1993 | Soltesz | 138/125 X |

FOREIGN PATENT DOCUMENTS

| 60-44002 | 3/1985 | Japan. | |
| 61-254918 | 11/1986 | Japan. | |
| 0042621 | 2/1989 | Japan | 385/117 |

Primary Examiner—Richard J. Apley
Assistant Examiner—Donna L. Maraglio
Attorney, Agent, or Firm—Sandler Greenblum & Bernstein

[57] ABSTRACT

An endoscope having a bendable portion that is connected to the distal end of a flexible insert tube constituting an insert part of the endoscope, the bendable portion being bendable as desired by remote control, a solid-state image pickup device that is disposed in a distal end block connected to the distal end of the bendable portion, and a signal cable that is connected to the solid-state image pickup device and extended through the bendable portion and the flexible insert tube. The endoscope includes a flexible tube that covers the signal cable in both the bendable portion and the flexible insert tube, and a braid tube that covers the outer surface of the flexible tube in the bendable portion.

21 Claims, 9 Drawing Sheets

ENDOSCOPE

BACKGROUND OF THE INVENTION

The present disclosure relates to subject matter contained in Japanese patent application No. 3-255287 (filed on Oct. 2, 1991), Japanese patent application No. 3-256279 (filed on Oct. 3, 1991), Japanese patent application No. 3-256280 (filed on Oct. 3, 1991), Japanese patent application No. 3-271613 (filed on Oct. 21, 1991), Japanese patent application No. 4-228112 (filed on Aug. 27, 1992) and Japanese patent application No. 4-228113 (filed on Aug. 27, 1992), which are expressly incorporated herein by reference in their entireties.

1. Field of the Invention

The present invention relates to an endoscope having a solid-state image pickup device which is disposed in the distal end portion of an insert part thereof.

2. Description of the Prior Art

In general, a signal cable that is connected to a solid-state image pickup device disposed in the distal end portion of an insert part of an endoscope is covered with a flexible tube of a synthetic resin material in both a bendable portion and a flexible insert tube that constitutes the insert part.

In the bendable portion, however, the wall thickness of the flexible tube cannot be increased without restriction. Accordingly, the signal cable, which is merely covered with the flexible tube, must unavoidably be limp.

For this reason, it is likely that the signal cable will become curled in the bendable portion while the bendable portion is repeatedly bent with a small radius of curvature, and it will locally press other built-in components, e.g., a light guide fiber bundle for illumination, causing them to break down early.

In addition, if the signal cable is inferior in surface slip characteristics, it may damage other components incorporated in the flexible insert tube.

Under these circumstances, a prior art device, as shown for example in FIG. 7, has been arranged such that a signal cable is covered with thin, porous tetrafluoroethylene resin tape 91, which has superior slip properties and high flexibility, by winding the tape 91 double around the cable, and in the portion of the signal cable which is located in the bendable portion the tape 91 is tied tightly with thread 93, as shown in FIG. 8, thereby preventing the tape 91 from coming loose. In FIGS. 7 and 8, reference numeral 92 denotes signal wires, and 94 shielding wires which are provided around the signal wires 92.

However, since the porous tetrafluoroethylene resin tape 91 tears relatively easily, it is likely that the tape 91 will catch on a bending mechanism or other associated component and tear while the bendable portion is bent repeatedly, as shown in FIG. 9, causing the shielding and signal wires 94 and 92 to be exposed, resulting in electrical leakage.

SUMMARY OF THE INVENTION

An object of the present invention is to provide an endoscope which is designed so that a signal cable that is connected to a solid-state image pickup device will not damage other built-in components, e.g., a light guide fiber bundle for illumination, in a bendable portion and a flexible insert tube constituting the insert part of the endoscope.

Another object of the present invention is to provide an endoscope having good durability, which is designed so that even if a bendable portion of the endoscope is bent repeatedly, the covering of a signal cable will not be damaged in the bendable portion.

Other objects and advantages of the present invention will become apparent from the following detailed description of illustrated embodiments of the invention.

According to the present invention, there is provided an endoscope having a bendable portion that is connected to the distal end of a flexible insert tube constituting an insert part of the endoscope, the bendable portion being bendable as desired by remote control, a solid-state image pickup device that is disposed in a distal end block connected to the distal end of the bendable portion, and a signal cable that is connected to the solid-state image pickup device and extended through the bendable portion and the flexible insert tube. The endoscope includes a flexible tube that covers the signal cable in both the bendable portion and the flexible insert tube, and a braid tube that covers the outer surface of the flexible tube in the bendable portion.

In addition, there is provided an endoscope having a bendable portion that is connected to the distal end of a flexible insert tube constituting an insert part of the endoscope, the bendable portion being bendable as desired by remote control. A solid-state image pickup device is disposed in a distal end block connected to the distal end of the bendable portion, and a signal cable is connected to the solid-state image pickup device and extended through the bendable portion and the flexible insert tube. The endoscope includes a flexible tube that covers the signal cable in the bendable portion, a spiral groove that is formed in the outer periphery of the flexible tube, and a coil spring that is fitted in the spiral groove.

In addition, there is provided an endoscope having a bendable portion that is connected to the distal end of a flexible insert tube constituting an insert part of the endoscope, the bendable portion being bendable as desired by remote control. A solid-state image pickup device is disposed in a distal end block connected to the distal end of the bendable portion, and a signal cable is connected to the solid-state image pickup device and extends through the bendable portion and the flexible insert tube. The endoscope includes a braid tube that covers the signal cable in the bendable portion, and a flexible tube that covers the braid tube by sticking fast to it from the outside thereof.

In addition, there is provided an endoscope having a bendable portion that is connected to the distal end of a flexible insert tube constituting an insert part of the endoscope. The bendable portion is bendable as desired by remote control, and a solid-state image pickup device is disposed in a distal end block connected to the distal end of the bendable portion. A signal cable is connected to the solid-state image pickup device and extends through the bendable portion and the flexible insert tube. The endoscope includes a flexible tube that covers the signal cable in the bendable portion, and porous tetrafluoroethylene resin tape that covers the signal cable in the flexible insert tube except for the portion that is covered with the flexible tube.

In addition, there is provided an endoscope having a bendable portion that is connected to the distal end of a flexible insert tube constituting an insert part of the endoscope. The bendable portion is bendable as desired by remote control, and a solid-state image pickup device is disposed in a distal end block connected to the distal end of the bendable portion. A signal cable that is connected to the solid-state image pickup device and extends through the bendable portion and the flexible insert tube. The endoscope includes a first flexible tube that covers the signal cable in the flexible insert tube, and a second flexible tube that covers the signal cable in the bendable portion, the second flexible tube having a lower flexibility than that of the first flexible tube.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
FIG. 1 is a sectional side view of a first embodiment of the present invention.

FIG. 1 shows an insert part of an endoscope according to a first embodiment of the present invention. A bendable portion 6 is connected to the distal end of a flexible insert tube 3 that constitutes the insert part. The bendable portion 6 is capable of being bent as desired by remote control. A distal end block 2 is connected to the distal end of the bendable portion 6. The distal end block 2 incorporates an objective lens 1 and other necessary components. Reference numeral 4 denotes a lens frame. In FIG. 1, detailed illustration of the bending mechanism is omitted.

A solid-state image pickup device 7 is disposed at the imagery position of the objective lens 1 in the distal end block 2. The solid-state image pickup device 7 is attached to a frame member 8, which is surrounded by an electrical insulating member 9.

A signal cable 10 comprises a plurality of signal wires 11 which are connected to the solid-state image pickup device 7 to input and output signals. The signal cable 10 extends through the bendable portion 6 and the flexible insert tube 3 over the entire length thereof. The signal wires 11 are surrounded by shielding wires 12. Each signal wire 11 is connected to a circuit board 7a of the solid-state image pickup device 7.

The outside of the shielding wires 12 of the signal cable 10 is covered with a flexible tube 13 over the entire length thereof. The flexible tube 13 is made of a synthetic resin material, e.g., polyurethane, vinyl chloride or nylon resin.

Further, the signal cable 10 is covered with a braid tube 14 which is placed in contact with the outer surface of the flexible tube 13 over the range from the distal end of the bendable portion 6 to a position in the flexible insert tube 3 which is slightly inward of the distal end thereof. The braid tube 14 is formed by braiding extra-fine metal wire, e.g., stainless steel wire, tungsten wire, or titanium alloy wire, into a tubular shape. The braid tube 14 is tied tightly to the flexible tube 13 with thread 15 at both ends thereof.

In addition, the meshes of the braid tube 14 are filled with an elastic potting compound 16 comprising silicone rubber, for example, thereby preventing dislocation of the meshes of the braid tube 14 and enhancing the adhesion of the braid tube 14 to the flexible tube 13.

Thus, since the flexible tube 13 is covered tightly with the braid tube 14, the signal cable 10 can endure twisting and is completely prevented from elongating. Further, since the meshes of the braid tube 14 are filled with the potting compound 16, the tight covering condition of the braid tube 14 is stabilized even more effectively.

Although other built-in components, e.g., a light guide fiber bundle for illumination, and tubes, are also inserted in the bendable portion 6 and the flexible insert tube 3, illustration thereof is omitted.

In the endoscope arranged as described above, the flexible tube 13 that covers the signal cable 10 in the bendable portion 6 is covered with the braid tube 14. Therefore, the signal cable 10 is sufficiently firm and unlikely to become curled even if the bendable portion 6 is repeatedly bent.

Since the meshes of the braid tube 14 are filled with the potting compound 16, the firmness of the signal cable 10 is enhanced, making it more unlikely to become curled. Accordingly, even if the bendable portion 6 is bent, the signal cable 10 will not press or get entangled in the illumination light guide fiber bundle or other built-in components.

Further, since the braid tube 14 is made of a metallic material, the surface thereof has excellent slip characteristics in comparison with ordinary flexible tubes. There is therefore only a slight possibility that the braid tube 14 will damage other built-in components by rubbing.

Figure 2:
FIG. 2 is a sectional side view of a second embodiment of the present invention.

Referring to FIG. 2, which shows a second embodiment of the present invention, the outside of shielding wires 22 that surround signal wires 21 of a signal cable 20 is covered tightly with a double layer of porous tetrafluoroethylene resin tape 23 over substantially the entire length of the flexible insert tube 3 winding two spiral strips of tape 23 thereon in two layers and in opposite directions without a gap between each pair of adjacent turns of each strip.

However, the tape 23 is stripped off over the range from the distal end of the bendable portion 6 to a position in the flexible insert tube 3 which is slightly inward of the distal end thereof, but the shielding wires 22 are covered with a flexible tetrafluoroethylene resin tube 25 instead at the portion stripped of the tape 23.

Further, the respective end portions of the tape 23 and the tube 25, including the joint of the tape 23 and the tube 25, are each tied tightly with thread 26 and secured to the underlying shielding wires 22 by using an adhesive (not shown).

The outer periphery of the tube 25 is formed with a spiral groove 27 having a semicircular cross-sectional configuration over the entire length thereof. A coil spring 28 which is made of stainless steel wire, for example, is fitted in the spiral groove 27. Further, the gap defined in the spiral groove 27 is filled with a potting compound 29.

In the endoscope having the above-described arrangement, the portion of the signal cable 20 which extends through the bendable portion 6 is covered with the tetrafluoroethylene resin tube 25, which has relatively high strength. Therefore, even if the bendable portion 6 is repeatedly bent over a long time, there is no likelihood that the covering of the signal cable 20 will be damaged by the bending mechanism or other associated components.

Further, since the tube 25 is spirally surrounded with the coil spring 28, the signal cable 20 will not buckle nor become curled even if the wall thickness of the tube 25 is reduced. There is therefore no possibility of the signal cable 20 damaging other built-in components in the bendable portion 6. In addition, since the coil spring 28 is fitted in the spiral groove 27 formed in the outer periphery of the tube 25 and the gap defined in the spiral groove 27 is filled with the elastic potting compound 29, there is no likelihood that the coil spring 28 will slip off or come out of the spiral groove 27.

Further, in the portion other than the bendable portion 6, the signal cable 20 is covered with the elastic tape 23 having excellent slip characteristics over substantially the entire length of the flexible insert tube 3. Therefore, there is no possibility of the signal cable 20 damaging other built-in components in the flexible insert tube 3, either. Since the tape 23 is wound double without a gap, there is no likelihood that both of the two layers of tape 23 will be loosened so as to ride up by bending of the flexible insert tube 3, which is bent with a much larger radius of curvature than that of the bendable portion 6.

Figure 3:
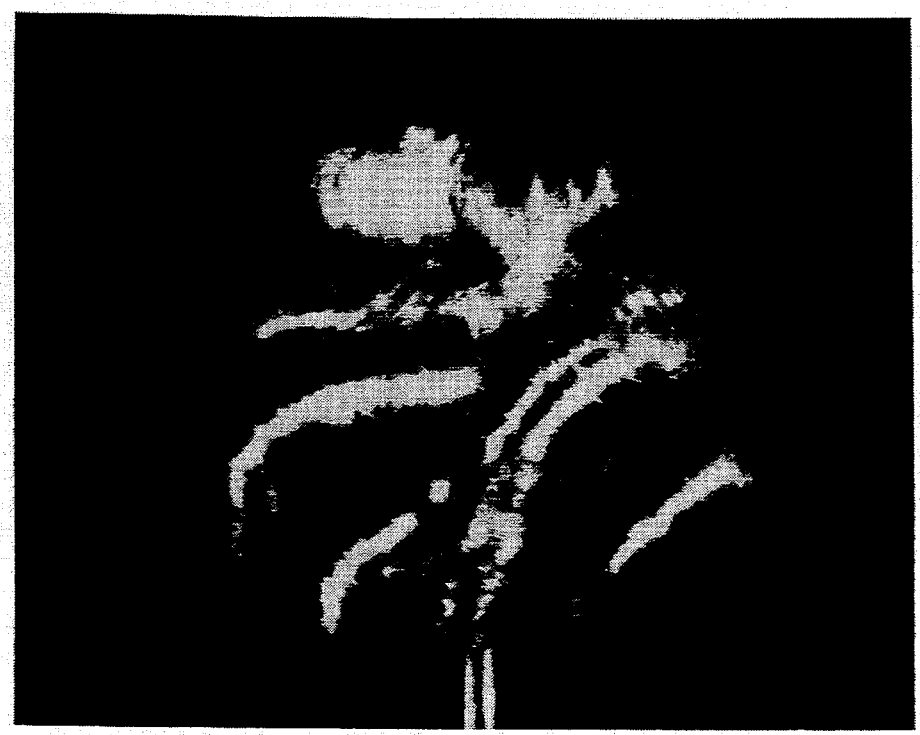
FIG. 3 is a sectional side view of a third embodiment of the present invention.

Referring to FIG. 3, which shows a third embodiment of the present invention, the portion of the signal cable 20 in the second embodiment which extends through the flexible insert tube 3 is covered with an elastic tube 33 formed of polyurethane resin, vinyl chloride resin, etc. in place of the double tape 23, thereby forming a signal cable 30. This arrangement also prevents damage to the signal cable 30 in the bendable portion 6.

Figure 4:
FIG. 4 is a sectional side view of a fourth embodiment of the present invention.

Referring to FIG. 4, which shows a fourth embodiment of the present invention, the outside of shielding wires 42 that surround signal wires 41 of a signal cable 40 is covered with a double layer of porous tetrafluoroethylene resin tape 43 over substantially the entire length of the flexible insert tube 3 by spirally winding two strips of tape 43 thereon in two layers and in opposite directions.

However, the tape 43 is stripped off over the range of from the distal end of the bendable portion 6 to a position in the flexible insert tube 3 which is slightly inward of the distal end thereof, but the shielding wires 42 are covered double with a braid tube 44 and a tube 45 instead at the portion stripped of the tape 43.

The braid tube 44 is formed by braiding extrafine metal wire, e.g., stainless steel wire, or tungsten wire, into a tubular shape. The tube 45 is formed by using a flexible, electrical insulating synthetic resin material, e.g., polyurethane, vinyl chloride or nylon resin.

The inner surface of the tube 45 is placed in close contact with the outer peripheral surface of the braid tube 44, and the rear end portion of the tube 45 is brought into close contact with the outer peripheral surface of the shielding wires 42 and butted against the forward end of the double tape 43. The butt joint portion is externally coated with a silicone rubber adhesive. The respective forward end portions of the tube 45 and the tape 43 are tied tightly to the signal cable 40 with thread 46 and then secured with the adhesive 47.

In the endoscope arranged as described above, the portion of the signal cable 40, which extends through the bendable portion 6, is covered with the durable tube 45 having neither roughness nor irregularities on the surface thereof, and the mechanical strength of the signal cable 40 is reinforced with the braid tube 44 provided inside the tube 45. Accordingly, the covering of the signal cable 40 will not be damaged by the bending mechanism or other associated component even if the bendable portion 6 is repeatedly bent over a long time.

Further, since in the portion other than the bendable portion 6, the signal cable 40 is covered with the elastic tape 43 having excellent slip characteristics over substantially the entire length of the flexible insert tube 3, there is also no possibility of the signal cable 40 damaging other built-in components in the flexible insert tube 3. Since the tape 43 is wound double without a gap, there is no likelihood that both of the two layers of tape 43 will be loosened to ride up by bending of the flexible insert tube 3, which is bent with a much larger radius of curvature than that of the bendable portion 6.

Figure 5:
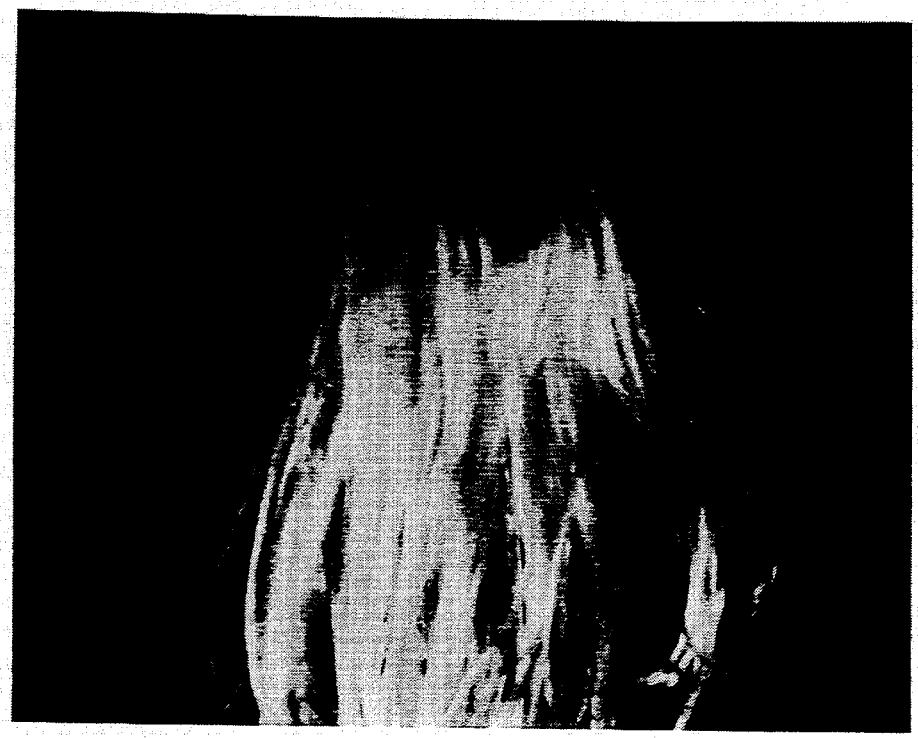
FIG. 5 is a sectional side view of a fifth embodiment of the present invention.

Referring to FIG. 5, which shows a fifth embodiment of the present invention, the portion of the signal cable 40 in the fourth embodiment which extends through the flexible insert tube 3 is covered with an elastic tube 53 formed of polyurethane resin, vinyl chloride resin, etc. in place of the double tape 43, thereby forming a signal cable 50. This arrangement also prevents damage to the signal cable 50 in the bendable portion 6.

Figure 6:
FIG. 6 is a sectional side view of a sixth embodiment of the present invention.
Figure 7:
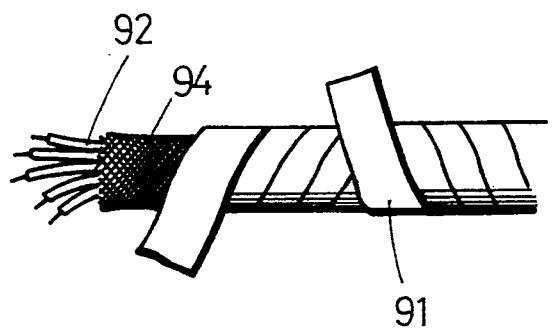
FIGS. 7, 8 and 9 are side views of a signal cable of a prior art device.
Figure 8:
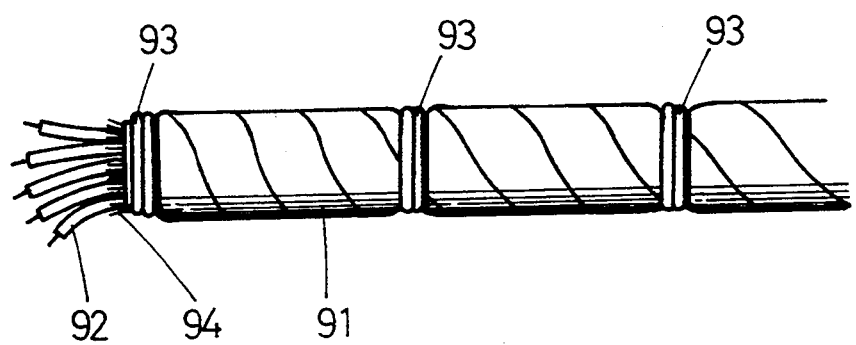
Figure 9:
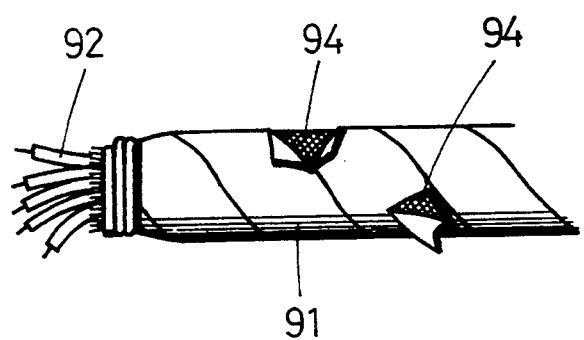
Figure 1:
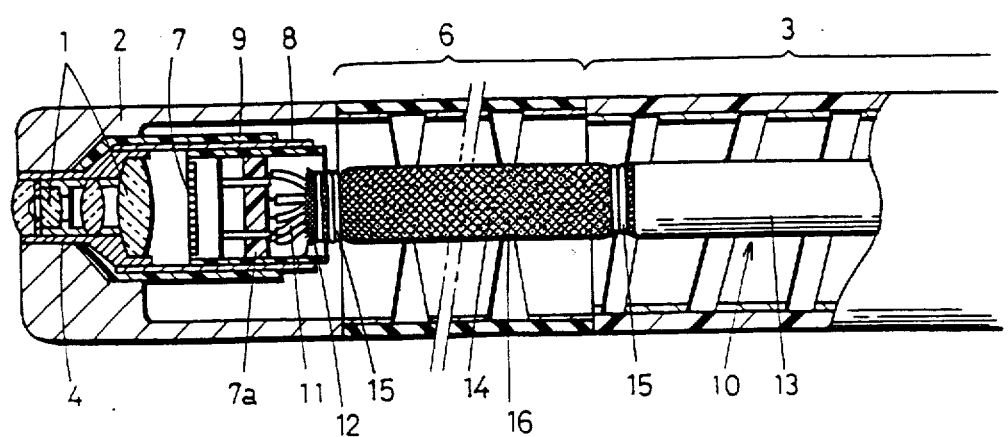
Figure 2:
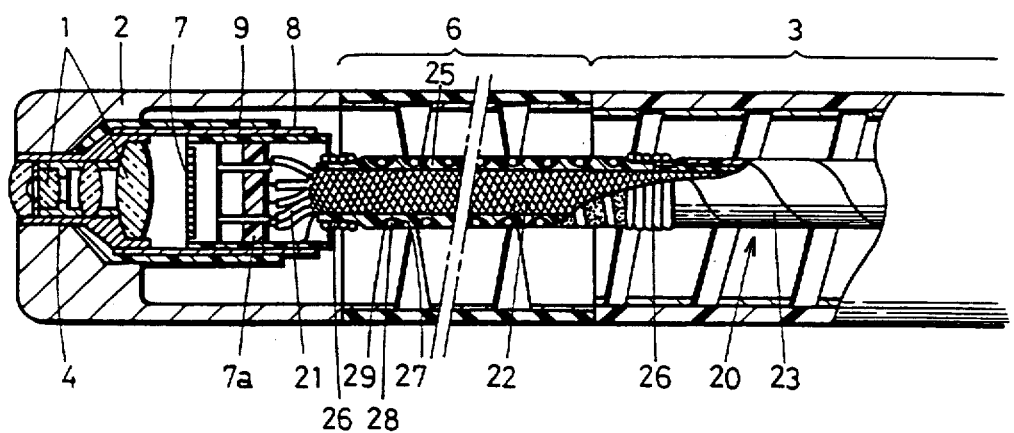
Figure 3:
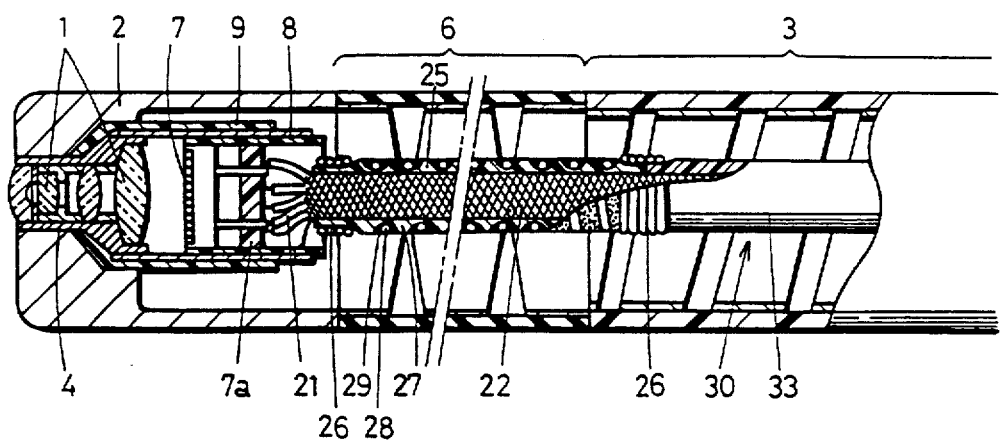
Figure 4:
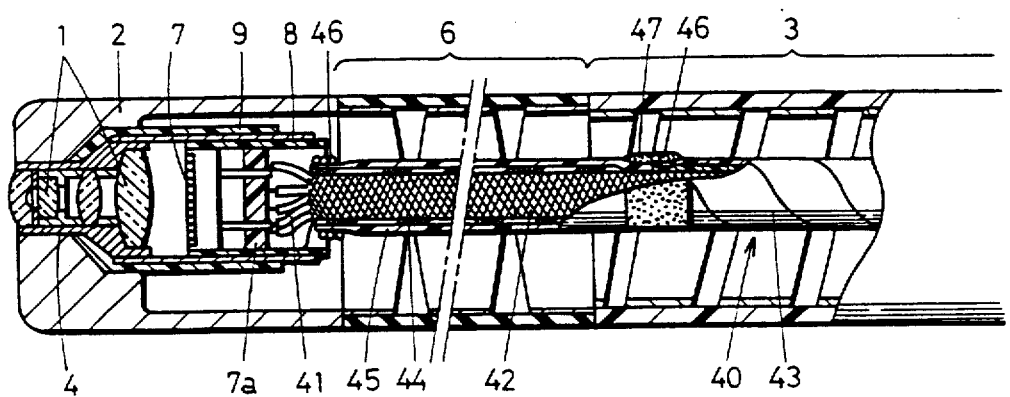
Figure 5:
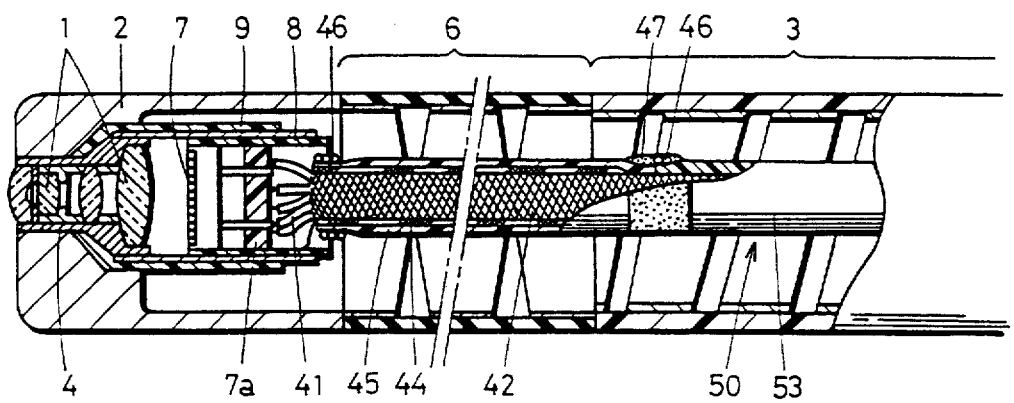
Figure 6:
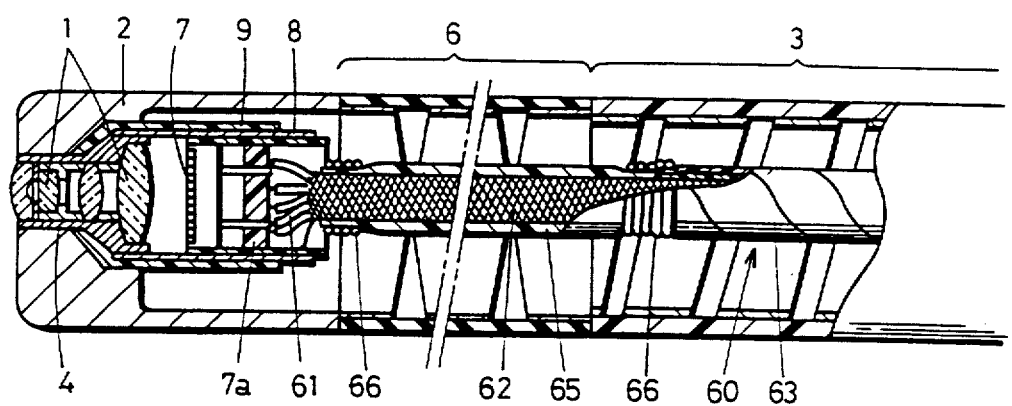

Referring to FIG. 6, which shows a sixth embodiment of the present invention, the outside of shielding wires 62 that surround signal wires 61 of a signal cable 60 is covered with a double layer of porous tetrafluoroethylene resin tape 63 over substantially the entire length of the flexible insert tube 3 by winding two strips of tape 63 thereon in two spiral layers and in opposite directions.

However, the tape 63 is stripped off over the range from the distal end of the bendable portion 6 to a position in the flexible insert tube 3 which is slightly inward of the distal end thereof, but the shielding wires 62 are covered with a tube 65 instead at the portion stripped of the tape 63. The tube 65 is formed by using a flexible, electrical insulating synthetic resin material, e.g., polyurethane, vinyl chloride or nylon resin.

Further, the respective end portions of the tape 63 and the tube 65, including the joint of the tape 63 and the tube 65, are each tied tightly with thread 66 and secured to the underlying shielding wires 62 by using an adhesive (not shown).

In the endoscope arranged as described above, the portion of the signal cable 60, which extends through the bendable portion 6, is covered with the durable tube 65 having neither roughness nor irregularities on the surface thereof. There is therefore no likelihood that the covering of the signal cable 60 will be caught in and damaged by the bending mechanism or other associated components even if the bendable portion 6 is repeatedly bent over a long time.

Further, since in the portion other than the bendable portion 6, the signal cable 60 is covered with the elastic tape 63 having excellent slip characteristics over substantially the entire length of the flexible insert tube 3, there is also no possibility of the signal cable 60 damaging other built-in components in the flexible insert tube 3. Since the tape 63 is wound double, there is no likelihood that both of the two layers of tape 63 will be loosened to ride up by bending of the flexible insert tube 3, which is bent with a much larger radius of curvature than that of the bendable portion 6.

According to the present invention, the signal cable is unlikely to become curled in the bendable portion of the endoscope. Therefore, it is possible to prevent damage to other built-in components in the bendable portion. Furthers since the mechanical strength of the signal cable is improved, it is possible to prevent damage to the covering of the signal cable in the bendable portion.

In addition, in the flexible insert tube of the endoscope the surface of the signal cable is arranged to be slippery, thereby preventing damage to other built-in components in the flexible insert tube.

While the invention has been described by reference to specific embodiments chosen for purposes of illustration, it should be apparent that numerous modifications could be made thereto by those skilled in the art without departing from the basic concept and scope of the invention.

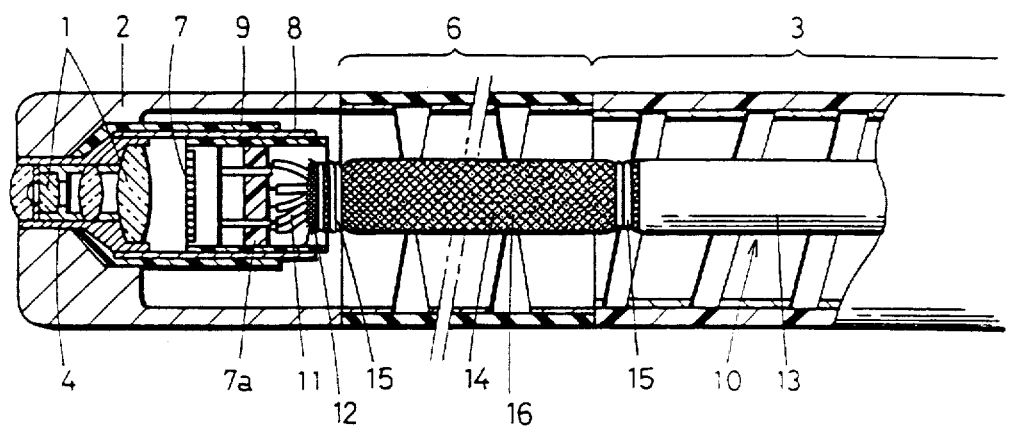

We claim:

1. An endoscope comprising a bendable portion that is connected to a distal end of a flexible insert tube constituting an insert part of said endoscope, said bendable portion being bendable as desired by remote control, a solid-state image pickup device being disposed in a distal end block connected to a distal end of said bendable portion, and a signal cable adapted to input and output signals being connected to said solid-state image pickup device and extending through said bendable portion and said flexible insert tube, said endoscope being a video endoscope and further comprising:
   a flexible tube that covers said signal cable in both said bendable portion and said flexible insert tube; and
   a braid tube that covers an outer surface of said flexible tube from the distal end of said bendable portion through a distal portion of said flexible insert tube, wherein part of the signal cable is covered flexible tube and another part is covered with the flexible tube and with the braid tube.

2. An endoscope according to claim 1, wherein the distal and proximal ends of said braid tube are secured to said signal cable.

3. An endoscope according to claim 1, wherein said braid tube is formed by braiding metallic small-gauge wire into a tubular shape.

4. An endoscope according to claim 1, wherein said braid tube includes meshes, said meshes of said braid tube being filled with a potting compound.

5. An endoscope comprising a bendable portion that is connected to a distal end of a flexible insert tube constituting an insert part of said endoscope, said bendable portion being bendable as desired by remote control, a solid-state image pickup device being disposed in a distal end block connected to a distal end of said bendable portion, and a signal cable adapted to input and output signals being connected to said solid-state image pickup device and extending through said bendable portion and said flexible insert tube, said endoscope being a video endoscope and further comprising:
   a flexible tube that covers said signal cable from the distal end of said bendable portion through a distal portion of said flexible insert tube,
   a spiral groove that is formed in an outer periphery of said flexible tube;
   a coil spring that is fitted in said spiral groove; and,
   porous tetrafluoroethylene resin tape that covers said signal cable in said flexible insert tube except for the portion that is covered by said flexible tube.

6. An endoscope according to claim 5, wherein the distal and proximal ends of said flexible tube are secured to said signal cable.

7. An endoscope according to claim 5, wherein said flexible tube is formed of a tetrafluoroethylene resin material.

8. An endoscope according to claim 5, wherein a gap is defined in said groove said gap being filled with a potting compound.

9. An endoscope according to claim 5, wherein said tape is wound double on an outer surface of said signal cable by winding two strips of porous tetrafluoroethylene resin tape in two spiral layers and in opposite directions.

10. An endoscope comprising a bendable portion that is connected to a distal end of a flexible insert tube constituting an insert part of said endoscope, said bendable portion being bendable as desired by remote control, a solid-state image pickup device being disposed in a distal end block connected to a distal end of said bendable portion, and a signal cable adapted to input and output signals being connected to said solid-state image pickup device and extending through said bendable portion and said flexible insert tube, said endoscope being a video endoscope and further comprising:
   a braid tube that directly covers said signal cable only from the distal end of said bendable portion through a distal portion of said flexible insert tube;
   a flexible tube that covers said braid tube by sticking fast to the outside of said braid tube.

11. An endoscope according to claim 10, wherein the distal and proximal ends of said flexible tube are secured to said signal cable.

12. An endoscope according to claim 10, further comprising porous tetrafluoroethylene resin tape that covers said signal cable in said flexible insert tube except for the portion that is covered by said braid tube.

13. An endoscope according to claim 12, wherein said tape is wound double on an outer surface of said signal cable by winding two strips of porous tetrafluoroethylene resin tape in two spiral layers and in opposite directions.

14. An endoscope according to claim 10, further comprising an elastic tube that covers said signal cable in said flexible insert tube except for the portion that is covered with said braid tube.

15. An endoscope having a bendable portion that is connected to a distal end of a flexible insert tube constituting an insert part of said endoscope, said bendable portion being bendable as desired by remote control, a solid-state image pickup device being disposed in a distal end block connected to a distal end of said bendable portion, and a signal cable being connected to said solid-state image pickup device and extending through said bendable portion and said flexible insert tube, said endoscope comprising:
   a flexible tube that covers said signal cable from the distal end of said bendable portion through a distal portion of said flexible insert tube; and
   porous tetrafluoroethylene resin tape that covers said signal cable in said flexible insert tube except for the portion that is covered with said flexible tube.

16. An endoscope according to claim 15, wherein the distal and proximal ends of said flexible tube are secured to said signal cable.

17. An endoscope according to claim 15, wherein said tape is wound double on an outer surface of said signal cable by winding two strips of porous tetrafluoroethylene resin tape in two spiral layers and in opposite directions.

18. An endoscope comprising a bendable portion that is connected to a distal end of a flexible insert tube constituting an insert part of said endoscope, said bendable portion being bendable as desired by remote control, a solid-state image pickup device being disposed in a distal end block connected to a distal end of said bendable portion, and a signal cable adapted to input and output signals being connected to said solid-state image pickup device and extending through said bendable portion and said flexible insert tube, said endoscope being a video endoscope and further comprising:

a flexible tube that covers said signal cable from the distal end of said bendable portion through a distal portion of said flexible insert tube;

a spiral groove that is formed in an outer periphery of said flexible tube;

a coil spring that is fitted in said spiral groove; and an elastic tube that covers said signal cable in said flexible insert tube except for the portion that is covered by said flexible tube.

19. The endoscope according to claim 18, wherein the distal and proximal ends of said flexible tube are secured to said signal cable.

20. The endoscope according to claim 18, wherein said flexible tube is formed of a tetrafluoroethylene resin material.

21. The endoscope according to claim 18, wherein a gap is defined by said groove, said gap being filled with a potting compound.

* * * * *

UNITED STATES PATENT AND TRADEMARK OFFICE
CERTIFICATE OF CORRECTION

PATENT NO. : 5,370,108
DATED : December 6, 1994
INVENTOR(S) : Shizuharu Miura, et al It is certified that error appears in the above-indentified patent and that said Letters Patent is hereby corrected as shown below:

The title page should be deleted and substitute therefor the attached title page.

Delete Drawing Sheets 1-6, and substitute therefor the Drawing Sheets consisting of FIGS. 1-6, as shown on the attached pages.

Column 7, line 41, before "flexible", insert --with the--.

Signed and Sealed this

Third Day of October, 1995

Attest:

BRUCE LEHMAN

Attesting Officer     Commissioner of Patents and Trademarks

United States Patent [19]

Miura et al.

[11] Patent Number: 5,370,108
[45] Date of Patent: Dec. 6, 1994

[54] ENDOSCOPE

[75] Inventors: Shizuharu Miura; Takayuki Ogino; Hiroyuki Katsurada, all of Tokyo, Japan

[73] Assignee: Asahi Kogaku Kogyo Kabushiki Kaisha, Tokyo, Japan

[21] Appl. No.: 948,499

[22] Filed: Sep. 22, 1992

[30] Foreign Application Priority Data

| Oct. 2, 1991 | [JP] | Japan | 3-255287 |
| Oct. 3, 1991 | [JP] | Japan | 3-256279 |
| Oct. 3, 1991 | [JP] | Japan | 3-256280 |
| Oct. 21, 1991 | [JP] | Japan | 3-271613 |
| Aug. 27, 1992 | [JP] | Japan | 4-228112 |
| Aug. 27, 1992 | [JP] | Japan | 4-228113 |

[51] Int. Cl.⁵ ............... A61B 1/00; A61B 1/04
[52] U.S. Cl. ........................ 128/4; 128/6; 385/118
[58] Field of Search ......... 385/118, 117; 606/15, 606/16, 19; 138/130, 133, 125; 128/4, 6

[56] References Cited

U.S. PATENT DOCUMENTS

| 3,417,745 | 12/1968 | Sheldon | 385/117 X |
| 3,572,325 | 3/1971 | Bazell et al. | 128/6 |
| 3,691,001 | 9/1972 | Takahashi et al. | |
| 3,788,304 | 1/1974 | Takahashi | 385/118 X |
| 3,799,151 | 3/1974 | Fukaumi et al. | 128/4 X |
| 3,855,897 | 12/1974 | Takahashi et al. | |
| 4,236,509 | 12/1980 | Takahashi et al. | 128/4 |
| 4,279,245 | 7/1981 | Takagi et al. | 128/4 |
| 4,327,711 | 5/1982 | Takagi | 128/4 |
| 4,699,463 | 10/1987 | D'Amelio et al. | 385/118 |
| 4,708,434 | 11/1987 | Tsuno | 385/118 |
| 4,784,464 | 11/1988 | Ouchi | |
| 4,899,787 | 2/1990 | Ouchi et al. | 128/4 X |
| 4,944,287 | 7/1990 | Takahashi et al. | |
| 4,979,498 | 12/1990 | Oneda et al. | 128/6 |
| 5,058,568 | 10/1991 | Irion et al. | 128/4 |
| 5,073,048 | 12/1991 | Adachi et al. | |
| 5,254,107 | 10/1993 | Soltesz | 138/125 X |

FOREIGN PATENT DOCUMENTS

| 60-44002 | 3/1985 | Japan . | |
| 61-254918 | 11/1986 | Japan . | |
| 0042621 | 2/1989 | Japan | 385/117 |

*Primary Examiner*—Richard J. Apley
*Assistant Examiner*—Donna L. Maraglio
*Attorney, Agent, or Firm*—Sandler Greenblum & Bernstein

[57] ABSTRACT

An endoscope having a bendable portion that is connected to the distal end of a flexible insert tube constituting an insert part of the endoscope, the bendable portion being bendable as desired by remote control, a solid-state image pickup device that is disposed in a distal end block connected to the distal end of the bendable portion, and a signal cable that is connected to the solid-state image pickup device and extended through the bendable portion and the flexible insert tube. The endoscope includes a flexible tube that covers the signal cable in both the bendable portion and the flexible insert tube, and a braid tube that covers the outer surface of the flexible tube in the bendable portion.

21 Claims, 9 Drawing Sheets